United States Patent [19]

Ertel et al.

[11] Patent Number: 5,691,352
[45] Date of Patent: Nov. 25, 1997

[54] STABLE PHARMACEUTICAL COMPOSITION OF TERFENADINE AND IBUPROFEN

[75] Inventors: Keith D. Ertel, West Chester, Ohio; David F. Long, Carmel, Ind.

[73] Assignee: Merrell Pharmaceuticals Inc., Cincinnati, Ohio

[21] Appl. No.: 624,362

[22] PCT Filed: Sep. 28, 1994

[86] PCT No.: PCT/US94/10972

§ 371 Date: Jul. 3, 1996

§ 102(e) Date: Jul. 3, 1996

[87] PCT Pub. No.: WO95/11677

PCT Pub. Date: May 4, 1995

Related U.S. Application Data

[63] Continuation of Ser. No. 142,528, Oct. 25, 1993, abandoned.

[51] Int. Cl.$^6$ ............................................. A61K 31/445
[52] U.S. Cl. .................................. 514/317; 514/970
[58] Field of Search ................................ 514/970, 317

[56] References Cited

U.S. PATENT DOCUMENTS

| | | | |
|---|---|---|---|
| 4,254,129 | 3/1981 | Carr et al. | 424/267 |
| 4,285,957 | 8/1981 | Carr et al. | 424/267 |
| 4,999,226 | 3/1991 | Schock et al. | 424/472 |
| 5,512,300 | 4/1996 | Weng et al. | 514/970 |

*Primary Examiner*—James H. Reamer
*Attorney, Agent, or Firm*—Michael J. Sayles

[57] ABSTRACT

The present invention is directed to a chemically stable pharmaceutical composition containing ibuprofen in combination with terfenadine, wherein the oxidation of terfenadine to terfenadone is prevented by the presence in the composition of an α-hydroxy carboxylic acid.

3 Claims, No Drawings

5,691,352

STABLE PHARMACEUTICAL COMPOSITION OF TERFENADINE AND IBUPROFEN

The present application has an effective international filing date of Sep. 28, 1994 as application PCT/US94/10972 which designated the U.S. and entered the U.S. national phase on Mar. 28, 1996 under 35 USC 371 and was assigned Ser. No. 08/624,362, which is a continuation of application Ser. No. 08/142,528 filed on Oct. 25, 1993, now abandoned.

The present invention is directed to a chemically stable pharmaceutical composition containing ibuprofen in combination with terfenadine, wherein the oxidation of terfenadine to terfenadone is prevented by the presence in the composition of an α-hydroxy carboxylic acid.

BACKGROUND

As known to those skilled in the art, many of the products currently available for the treatment of the symptomatology associated with ailments such as the common cold, seasonal rhinitis, sinus headaches, sinusitis, etc., contain multiple therapeutic agents. Many of these products contain an antihistamine in combination with an analgesic. They can also contain a sympathomimetic decongestant. These combination products are convenient for the patient since they allow the patient to obtain relief from numerous symptoms without taking multiple medications.

A variety piperidinoalkanol derivatives possessing antihistaminic properties are disclosed in U.S. Pat. Nos. 3,878, 217, 4,254,129 and 4,285,957. Specifically included within the scope of these patents is α-[4-(1,1-dimethylethyl) phenyl]-4-(hydroxydiphenylmethyl)-1-piperidinebutanol, known by its generic name terfenadine. This agent is commercially available and has experienced widespread acceptance by consumers and can be used according to the present invention as the free compound or as a pharmaceutically acceptable salt thereof as described in the above patents.

Recently, attempts have been made to produce dosage forms which contain these piperidinoalkanol antihistamines in combination with other therapeutic agents.

The pharmaceutical literature contains numerous examples of compounds which interact in the solid state when mixed. This interaction often results in the degradation of one or more of the mixture's components. Terfenadine and ibuorofen are examples of compounds which undergo such an interaction. By itself, terfenadine is chemically and physically stable. When combined with the nonsteroidal anti-inflammatory agent ibuprofen, however, terfenadine exhibits both physical and chemical incompatibilities. Neither terfenadine nor ibuprofen is hygroscopic, yet mixtures begin to cake shortly after preparation when stored at room temperature. The primary manifestation is an increase in the rate at which terfenadine is oxidized to its major degradation product, terfenadone. Terfenadone production is inhibited when tartaric acid is added to the mixtures. Since tartaric acid possesses only mild reducing properties, it is likely that its ability to inhibit terfenadone production is due to something other than antioxidant action. Previously, we have shown that terfenadine forms acid-base salts with both ibuprofen and tartaric acid. Here we examine tartaric acid's ability and the ability of other carboxylic acids to inhibit the oxidation of terfenadine in the presence of ibuprofen.

SUMMARY OF THE INVENTION

The degradation of terfenadine to terfenadone in mixtures containing ibuprofen alone or ibuprofen and unsubstituted dicarboxylic acids follows a diffusion controlled model. Adding α-hydroxy carboxylic acids, however, inhibits terfenadone production in the mixtures and brings the topochemical degradation under kinetic control. These results, along with infared absorption data and physical considerations, suggest the formation of hydrogen bonded terfenadine-α-hydroxycarboxylic acid complexes. The inhibition of terfenadone production may be due to the involvement of terfenadine's secondary alcohol in the complex formation.

DETAILED DESCRIPTION OF THE INVENTION

A therapeutically effective antihistaminic amount of terfenadine is that amount which produces the desired antihistaminic response upon oral administration, and as known to those skilled in the art this amount can vary widely. Typically, the amount required to produce this result will vary from about 0.1 mg to about 140 mg. The preferred therapeutically effective antihistaminic amount will vary from about 20 mg to about 70 mg. The tablets will generally contain about 60 mg of terfenadine. In determining the therapeutically effective antihistaminic amount, a number of factors are considered, including but not limited to: the bioavailability characteristics of the pharmaceutical composition administered; the dose regimen selected; and other relevant circumstances.

As used in this application, the term "ibuprofen" refers to choose nonsteroidal anti-inflammatory agents described in U.S. Pat. No. 3,228,831 as well as pharmaceutically acceptable salts thereof, with 2-(p-isobutyl-phenyl)propionic acid being most preferred. The quantity of ibuprofen required to produce the desired analgesic and antipyretic effect can vary widely as known to those skilled in the art and is affected by the same parameters described above for the appropriate dosage of the antihistamine. Generally the amount required to produce this effect will be within the range of from about 25 to about 400 mg and more preferably be within the range of from about 100 to about 300 mg. Generally, though, the tablets will contain about 200 mg of ibuprofen. Commercially available ibuprofen granulations are acceptable for use in the present invention. A preferred ibuprofen composition is available from Mallinckrodt Inc., under the tradename, DCI-63®.

Topochemical reactions are an important determinant of stability in a number of pharmaceutical systems. For example, these types of reactions are responsible for the increased rate of aspirin degradation observed when the compound is combined with phenylephrine hydrochloride, sodium bicarbonate (E. Nelson, et al., *Topochemical Decomposition Patterns of Aspirin, J. Pharm. Sci.,* 63, 755–57, 1974), magnesium stearate (P. V. Mroso, et al., *Solid—State Stability of Aspirin in the Presence of Excipients: Kinetic Interpretation, Modeling, and Prediction, J. Pharm. Sci.,* 71, 1096–1101, 1982) and mepyramine maleate (Li Wan Po, et al., *Drug—Drug Incompatibility in the Solid State: Kinetic Interpretation, Modeling, and Prediction, Int. J. Pharm.,* 18, 287–98, 1984). A number of geometric models have been developed to describe topochemical degradation kinetics, although in some cases the behavior predicted by these models is difficult to distinguish from a simple first-order decomposition pattern (J. T. Carsreason, et al., *Stability of Solid Dosage Forms, J. Pharm. Sci.,* 63, 1–14, 1974).

Preformulation studies were done and showed that dry mixtures of terfenadine and ibuprofen powders behaved similarly to the aspirin systems mentioned above: the degradation of terfenadine to its primary degradation product, terfenadone, was enhanced in the presence of ibuprofen. The degradation to terfenadone was inhibited, however, when tartaric acid was added to the mixtures. The following examines the solid-state interaction between terfenadine and carboxylic acids.

EXPERIMENTAL

Materials.

Terrenadine, terfenadone (U.S.P. and reference standard grades, Dow Chemical Company, Midland, Mich.), and ibuprofen (U.S.P. grade, Upjohn Pharmaceutical Company, Kalamazoo, Mich.) were used as received. The acids used included adipic acid, glutaric acid, malonic acid, succinic acid, tartronic acid (A.C.S. grade, Aldrich Chemical Company, Milwaukee, Wis.), glycolic acid (A.C.S. grade, Sigma Chemical Company, St. Louis, Mo.), and tartaric acid (commodity item).

Sample Preparation.

Mixtures of terfenadine and ibuprofen having an ibuprofen mole fraction of 0.93 were prepared by screening. One mixture served as a control and received no further treatment. Individual unsubstituted and hydroxy-substituted aliphatic carboxylic acids were incorporated into the remaining mixtures on an equimolar basis with terfenadine. Samples of each mixture were weighed into screw-capped vials and stored at 55° C. to accelerate terfenadone production.

Chromatographic Analysis.

Samples were dissolved in mobile solvent (acetnitrile/water/1M phosphate buffer, pH ca. 3.5/diethylamine, 500/394/100/6, v/v/v/v) and assayed for their terfenadine and terfenadone contents. The compounds were separated on a reversed-phase $C_{18}$ column (25 cm×4.6 mm i.d.) and quantified by measuring the UV absorbence of the column effluent at 254 nm. Peak areas in the sample chromatogram were converted to weights based on peak areas obtained from standard solutions of the pure materials analyzed under identical conditions.

Infrared Analysis.

Infrared analyses were performed using a Perkin Elmer 1800 Fourier Transform IR spectrophotometer yielding a band resolution of 4 $cm^{-1}$. Transmittance spectra were recorded for the pure materials and for mixtures of each carboxylic acid with terfenadine. The mixtures were prepared by screening and stored under ambient conditions until analyzed, usually within 2 weeks of preparation. Powder samples were mixed with spectroscopic grade potassium bromide, compressed into pellets, and scanned from 4000 $cm^{-1}$ to 500 $cm^{-1}$.

Results.

Microscopic examination of screened terfenadine powder showed it to be composed of cylindrical particles. If the reaction occurs on the cylinder's lateral surface and is not limited by diffusion of intact terfenadine through a decomposition product layer to reach the reaction interface, the topochemical degradation is described by:

$$1-(1-\alpha)^{1/2}=(k/r_0)t \quad (1)$$

where $\alpha$ is the fraction decomposed, $k$ is a degradtion rate constant, and $r_0$ is the initial radius of the cylinder. If, however, terfenadine must diffuse through a decomposition product layer to interact with ibuorofen, so-called Jander kinetics apply and the process is described by:

$$[1-(1-\alpha)^{1/2}]^2=(2k/r_0^2)t \quad (2)$$

The results of the data from the control mixture and the mixture containing tartaric acid were fitted to the above equations. Curvature is apparant when the control data are fitted to Equation 1, but a reasonably linear fit is obtained when the data are treated by Equation 2. Conversely, the data from the mixture containing tartaric acid are linearizod by Equation 1, but exhibit curvature when fitted to Equation 2. This implies that the rate limiting process of the topochemical degradation is different in the mixtures, i.e., the mechanism changes. A similar phenomenon was described previously for the topochemical degradation of aspirin, but temperature, rather than the addition of tartaric acid, was responsible for the change in that case.

The mechanistic change effected by adding tartaric acid to the mixture of terfenadine and ibuorofen was further examined by preparing mixtures containing various unsubstituted and hydroxy-substituted carboxylic acids. The results of fitting the kinetic data obtained from all of the mixtures to Equations 1 and 2 are reported in Table I.

TABLE I

SLOPES AND COEFFICIENTS OF DETERMINATION (CD) OBTAINED BY FITTING THE ACCELERATED STABILITY DATA FROM ALL MIXTURES TO EQUATIONS 1 AND 2

| ACID ADDED | EQUATION 1 | | EQUATION 2 | |
|---|---|---|---|---|
| | Slope[a] | CD | Slope[a] | CD |
| None (control) | 43900 | 0.678 | 461 | 0.903 |
| Malonic | 93300 | 0.676 | 1040 | 0.855 |
| Succinic | 89900 | 0.815 | 957 | 0.949 |
| Glutaric | 151000 | 0.752 | 2670 | 0.961 |
| Adipic | 122000 | 0.744 | 1760 | 0.978 |
| Glycolic | 22300 | 0.938 | 110 | 0.740 |
| Tartronic | 4470 | 0.985 | 370 | 0.966 |
| Tartaric | 32600 | 0.947 | 337 | 0.815 |

[a]Slope × $10^9$

An interesting pattern is apparant when one compares the results obtained from mixtures containing unsubstituted dicarboxylic acids to those obtained from mixtures containing hydroxy-substituted carboxylic acids. The control mixture and all of the mixtures containing unsubstituted carboxylic acids are better fitted using Equation 2 (i,e. exhibit diffusion control) while all of the mixtures containing hydroxy-substituted carboxylic acids are better fitted using Equation 1 (i.e. exhibit kinetic control). This pattern strongly suggests that the inhibition of terfenadone production and the change in the limiting step of the topochemical degradation are due to the presence of alcohol functional groups on the acids.

Ibuprofen is known to form a solid-state salt with magnesium hydroxide (T. T. Kararli, et al., *Solid—State Interaction of Magnesium Oxide and Ibuprofen to Form a Salt, Pharm. Res.*, 6, 804–808, 1989). In addition, several of the dibasic acids used in this work have been shown to form solid-state complexes with caffeine and theophylline through an interaction between a carboxylic acid functional group and a xanthine ring nitrogen (J. Nishijo, et al., *The Interaction of Caffeine With Several Aliphatic Organic Dibasic Acids in the Solid State, Yakugaku Zasshi*, 100, 732–38, 1980 and J. Nishijo, et al., *The Interaction of Theophylline With Several Aliphatic Organic Dibasic Acids in the Solid State, Yakugaku Zasshi*, 103, 819–24, 1983). Similar interactions between the carboxylic acids used in this work and terfenadine were demonstrated by recording the infrared spectra of the acids alone and in combination with terfenadine. All of the spectra obtained from the mixtures exhibited frequency shifts in the position of the carboxylic acid carbonyl absorption band from its normal position at ca. 1700 cm$^{-1}$ to ca. 1600 cm$^{-1}$ (see Table II, below). This shift is due to a resonance between the carbonyl carbon and its associated oxygen atoms that occurs when the carboxylic acid functional group becomes perturbed or ionized (J. Lecomte, *Infrared Absorption Spectra of Metallic Acetyl—acetonates, Disc. Faraday Soc.*, 9, 125–131, 1950).

The shift in the carboxylic acid carbonyl absoroption band, coupled with the propensity of α-hydroxycarboxylic acids to form intermolecular hydrogen bonds in the solid state (M. D. Newton, et al., *Stereochemistry of the α-Hydroxycarboxylic Acids and Related Systems, J. Am. Chem. Soc.*, 99, 2413–21, 1977; C. E. Blom, et al., *Structure of Glycolic Acid Determined by Microwave Spectroscopy, J. Am. Chem. Soc.*, 104, 2993–96, 1982), may explain their ability to change limiting process of topochemical degradation. Terfenadone formation occurs when a secondary alcohol located δ- to a basic piperidine nitrogen is oxidized. Molecular modeling calculations show that the distance separating these groups is approximately 5 Å, which is of the same order of magnitude as the distance separating the carboxylic acid and alcohol functional groups in the α-hydroxycarboxylic acids. This, along with the carbonyl perturbation, suggests the formation of hydrogen bonded terfenadine-carboxylic acid complexes. Since the secondary alcohol of terfenadine would be tied up by such an interaction, the complexes should exhibit decreased susceptibility to reaction with ibuprofen. The unsubstituted carboxylic acids, lacking an α-hydroxy group, are unable to form such complexes with terfenadine and are thus unable to inhibit increased terfenadone production in the presence of ibuprofen.

We have shown that the position of the carbonyl absorbtion band in the infared spectra of ibuprofen and tartaric acid exhibits a frequency shift when the compounds are combined with terfenadine. The band normally appears near 1700 cm$^{-1}$, but is shifted nearer 1600 cm$^{-1}$ in the mixtures due to ionization of the carboxylic acid functional group. The ionization is most likely due to the formation of an acid-base salt between the carboxylic acid and the basic piperidine nitrogen of terfenadine, which has a reported pK$_a$ value of 8.58.

The oxidation of terfenadine to terfenadone occurs at a secondary alcohol group. This alcohol group is separated from the piperidine nitrogen by four carbon atoms, the same number of carbons in the tarzaric molecule. It was initially postulated that tartaric acid's ability to inhibit terfenadone production is due to the interaction of its two carboxylic acid groups with terfenadine, one forming the salt with the piperidine nitrogen, the other interacting with the 2° alcohol to inhibit its oxidation.

A series of samples was prepared containing terfenadine, ibuprofen, and various unsubstituted dicarboxylic acids ranging from $C_3$–$C_6$ in length. The infared spectra of all these acids showed the acid carbonyl frequency shift from ca. 1700 cm$^{-1}$ when the acids were combined with terfenadine (see Table II, below), indicating salt formation. The dicarboxylic acids are all stronger acids than ibuprofen, hence, they should interact preferentially with terfenadine in the mixtures to form salts.

TABLE II

INFRARED ABSORPTION FREQUENCIES OF THE CARBONYL FUNCTIONAL GROUP OF THE CARBOXYLIC ACIDS USED IN THIS STUDY

| SAMPLE | ABSORPTION FREQUENCY (cm$^{-1}$) | |
|---|---|---|
| | Carbonyl | Shift |
| Adipic Acid | | |
| alone | 1697 | |
| with terfenadine | 1694 | 1567 |
| Glutaric Acid | | |
| alone | 1698 | |
| with terfenadine | 1708 | 1568 |
| Glycolic | | |
| alone | 1731 | |
| with terfenadine | 1727 | 1602 |
| Malonic | | |
| alone | 1735 | |
| | 1706 (shoulder) | |
| with terfenadine | 1727 | 1598 |
| Succinic | | |
| alone | 1695 | |
| | 1729 (shoulder) | |
| with terfenadine | 1695 | 1576 |
| Tartaric | | |
| alone | 1740 | |
| with terfenadine | 1730 | 1610 |
| Tartronic | | |
| alone | 1743 | |
| with terfenadine | 1742 | 1619 |

The wavenumber values reported are for the acids alone and in equimolar mixtures with terfenadine If the interaction scheme proposed above for tartaric acid is correct, maximum inhibition of terfenadone production should occur in mixtures containing a dicarboxylic acid of the same chain length, i.e. succinic acid. The time course of terfenadone production in acid-containing and control mixtures is shown in FIG. 3. The data are not fitted to a kinetic model because of the small (although significant from a stability standpoint) amounts of terfenadone formed in the samples. The interaction hypothesis is obviously not correct, since terfenadone production is not inhibited by the dicarboxylic acids. In fact, the acids apparantly increase terfenadone production in the mixtures. The greater acidity of the dicarboxylic acids relative to ibuorofen may account for the increased terfenadone production in mixtures in which they are incorporated. Solution kinetic studies performed in mixed media have shown that terfenadone production is enhanced under acidic conditions. Although no liquid is added to the powder mixtures per se, there is apparantly a "liquid" phase formed due to the physical incompatability between terfenadine and ibuprofen. The dicarboxylic acids may lower the apparant pH of this phase, resulting in greater terfenadone production than in the control samples.

The tartaric acid molecule also has alcohol functional groups at the 2 and 3 positions. To test whether these groups are responsible for inhibiting terfenadone production, mixtures containing glycolic and tartronic acids were prepared. Both of these compounds form salts with terfenadine (see Table I, above), and both are stronger acids than ibuprofen. Samples containing tartaric acid were also prepared. As above, the data are not fitted to any kinetic model because of the relatively small amounts of terfenadone formed. Terfenadone levels in the samples containing the hydroxy substituted acids are lower than in the control samples for at least 60 days at 45° and at least 210 days at 55°. These data, in conjuction with the failure of the dicarboxylic (specifically, malonic and succinic) acids to inhibit terfenadone production, indicate that an interaction involving one of tartaric acid's hydroxy groups is responsible for inhibiting the oxidation of the secondary alcohol group of terfenadine. An interaction scheme similar to that described previously is likely, except that an alcohol functional group interacts with the secondary alcohol of terfenadine rather than a carboxylic acid group. This interaction, which likely involves hydrogen bonding, is relatively weak, as evidenced by the fact that terfenadone production is not completely inhibited by the addition of the hydroxy substituted acids.

Glycolic and tartronic acid are both monohydroxy carboxylic acids. Based on the stability of mixtures containing these acids and the fact that malonic acid does not inhibit terfenadone production, it appears that the hydroxy group located α- to the carboxylic acid group forming a salt with the piperidine nitrogen is responsible for interacting with the secondary alcohol of terfenadine. The maximum distance separating the acidic proton from the α-hydroxy proton in the carboxylic acid is estimated, using published bond lengths and angles, to be between 3 and 4 angstroms. Molecular modeling calculations show that the butyl chain separating the piperidine nitrogen and the 2° alcohol group of terfenadine is not fully extended, and that the distance separating these groups is approximately 5 Å. Hence, an interaction between the molecules involving these functional groups is not unreasonable from a dimensional standpoint.

All of the hydroxy substituted carboxylic acids inhibit terfenadine oxidation in the presence of ibuorofen to some degree. However, mixtures containing tartronic acid exhibit greater inhibition than mixtures containing glycolic or tartaric acids. This may be due to an inductive effect in the tartronic acid molecule. The alcohol group of this acid is attached to a carbon interposed between two carboxylic acid functional groups. This position may increase the acidity of the alcoholic proton, making it more available for interaction with the secondary alcohol of terfenadine.

Conclusion.

Tartaric acid inhibits terfenadone production in mixtures of terfenadine with ibuprofen. It was originally believed that the inhibition was due to an interaction between the two carboxylic acid groups of tartaric acid and the piperidine nitrogen and 2° alcohol group of terfenadine. Results from stability studies using various unsubstituted and hydroxy substituted carboxylic acids show that this explanation is not correct. There is an interaction between a carboxylic acid group and the piperidine nitrogen, but an α-hydroxy group, rather than the second carboxylic acid group, interacts with the secondary alcohol to inhibit its oxidation.

The topochemical degradation of terfenadine to terfenadone in the presence of ibuprofen is adequately described by models which assume a cylindrical particle geometry. Adding tartaric acid to the mixture inhibits terfenadone production and changes the reaction from one that is under diffusion control to one that is kinetically controlled. Similar results are obtained with other α-hydroxycarboxylic acids, but not with unsubstituted aliphatic acids. These results, along with infared spectroscopic data and physical considerations, suggest that the α-hydroxy acids may decrease terfenadone production by forming solid-state complexes with terfenadine, thereby inhibiting its reaction with ibuprofen.

A sample tablet formulation containing a 1:1 molar ratio of tartaric acid and terfenadine is presented in Table III.

TABLE III

TERFENADINE/PSEUDOPHEDRINE/IBUPROFEN
SINGLE LAYER TABLET FORMULATION FORMATION
1:1 Molar Ratio of Terfenadine/Tartaric Acid Formulation

| Component | Amount per Tablet mg. |
| --- | --- |
| Terfenadine | 30.0 |
| Pseudophedrine HCl | 60.0 |
| Cellulose microcrystalline | 104.5 |
| Starch | 60.0 |
| Polysorbate 80 | 5.3 |
| Ibuprofen 63% DC | 318.0 (200) |
| Starch Glycolate Sodium | 6.0 |
| Tartaric Acid | 9.5 |
| Talc | 10.0 |
| Tablet Weight | 603.3 |

The ingredients of the pharmaceutical composition of the present invention are brought together into a dosage form for oral administration according to standard practices and procedures well known in the pharmaceutical sciences using conventional formulation and manufacturing techniques. The terfenadine layer is wet granulated, dried and blended with lubricants according to techniques know in the art. The commercially available ibuprofen granulation is blended with lubricants. It is currently preferred that the triple layered tablet be manufactured utilizing a triple layer tablet press. Specific details regarding a pharmaceutical composition comprising terfenadine and ibuprofen are disclosed in U.S. Pat. No. 4,999,226, incorporated herein by reference. It will be recognized, however, that although this sample formulation is a triple formulation of terfenadine, ibuprofen and pseudophedrine, the principle of stabilizing a formulation of terfenadine and ibuprofen with an alpha-hydroxy carboxylic acid applies also to a formulation in which the pseudophedrine ingredient is absent.

The dosage range of these tablets can vary widely depending upon the amount of active ingredient contained within the dosage form, the particular medications incorporated into the dosage form, the patient, the severity of the patient's symptoms, etc. Typically though, the dose will be one or two tablets administered from 2 to 4 times daily.

As used in this application, the term "patients" refers to a warm blooded mammal such as, for example rabbits, mice, rats, guinea pigs, chimpanzees, humans, etc.

What is claimed is:

1. A chemically stable pharmaceutical composition comprising:

(a) a therapeutically effective analgesic amount of ibuprofen or a pharmaceutically acceptable salt thereof;

(b) a therapeutically effective antihistaminic amount of terfenadine or a pharmaceutically acceptable salt thereof; and, (c) a dicarboxylic acid.

2. A chemically stable pharmaceutical composition comprising:

(a) a therapeutically effective analgesic amount of ibuprofen or a pharmaceutically acceptable salt thereof;

(b) a therapeutically effective antihistaminic amount of terfenadine or a pharmaceutically acceptable salt thereof; and, (c) tartaric acid.

3. A chemically stable pharmaceutical composition comprising:

(a) a therapeutically effective analgesic amount of ibuprofen or a pharmaceutically acceptable salt thereof;

(b) a therapeutically effective antihistaminic amount of terfenadine or a pharmaceutically acceptable salt thereof; and, (c) tartronic acid.

* * * * *

UNITED STATES PATENT AND TRADEMARK OFFICE
CERTIFICATE OF CORRECTION

PATENT NO. : 5,691,352

DATED : November 25, 1997

INVENTOR(S) : Keith D. Ertel, et al.

It is certified that error appears in the above-identified patent and that said Letters Patent is hereby corrected as shown below:

At column 1, line 27, the patent reads "variety piperidinoalkanol" and should read --variety of piperidinoalkanol--.
At column 1, line 45, column 3, line 66, column 4, line 16, column 6, line 49, and column 7, line 36, the patent reads "ibuorofen" and should read --ibuprofen-- as found throughout the specification.
At column 2, line 29, the patent reads "choose nonsteroidal" and should read
--those nonsteroidal-- .
At column 2, line 64, the patent reads "Carsreason" and should read --Carstensen--.
At column 3, line 31, the patent reads "acetnitrile" and should read --acetonitrile--.
At column 4, line 7, the patent reads "linearizod" and should read --linearized--.
At column 5, line 21, the patent reads "of topochemical" and should read --of the topochemical--.
At column 5, line 39, the patent reads "absorbtion" and should read --absorption--.
At column 5, line 52, the patent reads "tarzaric" and should read --tartaric--.
At column 6, lines 47 and 54, the patent reads "apparantly" and should read --apparently--.
At column 7, line 27, the patent reads "angstroms" and should read --angstoms--.
At column 8, line 32, the patent reads "know" and should read --known--.

Signed and Sealed this

Twenty-ninth Day of December, 1998

Attest:

BRUCE LEHMAN

Attesting Officer

Commissioner of Patents and Trademarks